US010245360B2

(12) United States Patent
Andrus et al.

(10) Patent No.: US 10,245,360 B2
(45) Date of Patent: Apr. 2, 2019

(54) CONNECTOR RING CLAMP AND ASSOCIATED METHODS OF USE

(71) Applicant: HeartWare, Inc., Miami Lakes, FL (US)

(72) Inventors: Lance Lynn Andrus, Southborough, MA (US); Andre Castillo, Aventura, FL (US)

(73) Assignee: HeartWare, Inc., Miami Lakes, FL (US)

( * ) Notice: Subject to any disclaimer, the term of this patent is extended or adjusted under 35 U.S.C. 154(b) by 0 days.

(21) Appl. No.: 14/741,008

(22) Filed: Jun. 16, 2015

(65) Prior Publication Data
US 2015/0359952 A1 Dec. 17, 2015

Related U.S. Application Data

(60) Provisional application No. 62/013,156, filed on Jun. 17, 2014.

(51) Int. Cl.
*A61M 1/10* (2006.01)
*A61M 1/12* (2006.01)

(52) U.S. Cl.
CPC .......... *A61M 1/1008* (2014.02); *A61M 1/101* (2013.01); *A61M 1/122* (2014.02)

(58) Field of Classification Search
CPC .......... A61M 1/10; A61M 1/12; A61M 1/10; A61M 1/122
USPC ........................................................ 600/16
See application file for complete search history.

(56) References Cited

U.S. PATENT DOCUMENTS

| 4,078,556 | A | * | 3/1978 | Fahim ...................... A61F 6/02 128/842 |
| 6,146,325 | A | | 11/2000 | Lewis et al. |
| 2004/0171905 | A1 | | 9/2004 | Yu et al. |
| 2007/0134993 | A1 | | 6/2007 | Tamez et al. |
| 2007/0179558 | A1 | * | 8/2007 | Gliner ................ A61N 1/36082 607/45 |

(Continued)

FOREIGN PATENT DOCUMENTS

WO    2015061314 A1    4/2015

OTHER PUBLICATIONS

International Search Report and Written Opinion for Application No. PCT/US2015/036025 dated Sep. 22, 2015.

*Primary Examiner* — Catherine Voorhees
*Assistant Examiner* — Roland Dinga
(74) *Attorney, Agent, or Firm* — Christopher & Weisberg, P.A.

(57) ABSTRACT

In one embodiment, the present invention includes a connector ring assembly to attach a VAD to a heart. The assembly includes a clamp which can rotate completely about the annular wall in a first state and is fixed relative to the annular wall in a second state. The clamp transitions from the first state to the second state via an actuator. The actuator can be configured with an axis of rotation generally parallel to the opening of the annular wall, thereby allowing manipulation of the actuator through the same surgical accessway as that used to implant the connector ring assembly. At least one embodiment provides a connector flange separately from an annular wall to provide greater access to the connector flange during implantation. The annular wall and clamp are attached to the connector flange after the flange is fixed to the heart.

16 Claims, 12 Drawing Sheets

(56) References Cited

U.S. PATENT DOCUMENTS

| | | | |
|---|---|---|---|
| 2009/0069635 A1* | 3/2009 | Gephart | A61B 1/32 600/224 |
| 2009/0171136 A1 | 7/2009 | Shambaugh, Jr. | |
| 2010/0324644 A1* | 12/2010 | Levi | A61B 5/6882 607/133 |
| 2011/0118833 A1* | 5/2011 | Reichenbach | A61B 17/11 623/3.1 |
| 2012/0010455 A1 | 1/2012 | Reichenbach et al. | |
| 2012/0226096 A1* | 9/2012 | Callaway | A61M 1/10 600/16 |
| 2013/0178694 A1* | 7/2013 | Jeffery | A61M 1/12 600/16 |
| 2015/0112120 A1* | 4/2015 | Andrus | A61M 1/1008 600/16 |

* cited by examiner

CONNECTOR RING CLAMP AND ASSOCIATED METHODS OF USE

CROSS-REFERENCE TO RELATED APPLICATIONS

The present application claims the benefit of the filing date of U.S. Provisional Patent Application No. 62/013,156 filed Jun. 17, 2014, the disclosure of which is hereby incorporated herein by reference.

BACKGROUND OF THE INVENTION

The present invention relates to components and methods used in connection with ventricular assist device connectors.

In certain disease states, the heart lacks sufficient pumping capacity to meet the needs of the body. This inadequacy can be alleviated by providing a mechanical pump referred to as a ventricular assist device ("VAD") to supplement the pumping action of the heart. Considerable effort has been devoted to providing a VAD which can be implanted and which can remain in operation for months or years to keep the patient alive while the heart heals, or which can remain in operation permanently during the patient's lifetime if the heart does not heal, or which can keep the patient alive until a suitable donor heart becomes available.

The VAD is typically connected to the heart, most commonly to the left ventricle. Typically, one end of a tube is connected to the VAD and the other end is connected to the aorta. Once connected, the VAD and the heart both pump blood from the left ventricle to the ascending or descending aorta to improve blood flow. Alternatively, a VAD may be connected to the ventricle to assist the heart in pumping blood to into pulmonary arteries.

The VAD typically is connected to the heart through the use of a VAD connector, as disclosed in U.S. Published Patent Application Nos. 2004/0171905 and 2007/0134993, the disclosures of which are hereby incorporated by reference herein. The VAD connector may be in the shape of a ring and is attached to the outer surface of the heart, commonly through the use of sutures. A separate surgical tool is then used to cut a hole in the ventricle within the VAD connector. A tube extending from the VAD is inserted through another hole in the left ventricle. The VAD is then attached to the VAD connector such that in inlet tube of the VAD is positioned within the central opening of the VAD connector. The VAD connector is used to clamp the tube and thereby hold the VAD in position on the heart. In other procedures, another component of the VAD, such as a pump housing or other element, is inserted into the connector ring. To prevent hemorrhaging and other complications, the seal between the VAD and VAD connector must be sufficiently tight to prevent blood loss from the heart.

BRIEF SUMMARY OF THE INVENTION

A connector ring according to one aspect of the disclosure desirably includes an annular wall defining a first opening adapted to receive a conduit, the first opening having an opening axis; a clamp having a body engaging the annular wall and defining a second opening co-axial with the first opening; an actuator adapted to transition the clamp between a first state and a second state; wherein the clamp is adapted to rotate relative to the annular wall in the first state and is fixed relative to the annular wall in the second state. The actuator can move about an actuator axis generally parallel to, and may be offset from, the opening axis. In some embodiments, the clamp may also include a first arm and a second arm extending from the body, wherein the first arm and the second arm are separated by a distance in the first state and a reduced distance in the second state.

Another aspect of the disclosure includes a clamp having first and second arms extending from the body, wherein at least a portion of the first and second arms overlap. The first and second arm may form a unitary member which includes a flexible band. The diameter of the second opening defined by the clamp body in the first state may be larger than the outer diameter of the annular wall and the clamp may bear on the outer diameter of the annular wall in the second state. In some embodiments, a connecting ring may also include a spanning member adapted to receive the actuator and coupled to one of the first arm and the second arm and extending past the other of the first arm and the second arm. An actuator may comprise a cam rotatable about the actuator axis and rotation of the cam can urge one of the first arm and second arm toward the other of the first arm and the second arm. The actuator may have a sloping cam surface and can be threadingly engaged with the clamp body for movement along the actuator axis upon rotation of the cam about the actuator axis. The actuator may have an interface configured to engage a tool by relative motion of the tool and actuator along the actuator axis. The annular wall can comprise at least one relief cut extending from a proximal side toward a distal side of the annular wall wherein the relief cut has a first width when the clamp is in the first state and a second width smaller than the first width when the clamp is in the second state.

A connector ring assembly can include a brake formed separately from the clamp body adapted to be moved by the actuator to transition the clamp from the first state to the second state by moving the brake relative to the body to reduce the diameter of the second opening. The body may comprise first and second portions connected by at least one hinge.

A connector ring assembly may further comprise a gimbal adapted to be placed within the first opening to receive a conduit at a plurality of angles relative to the opening axis.

A method of installing a connector ring according to one aspect of the disclosure can include securing a connector ring having an annular wall defining a first opening to tissue, the first opening having an opening axis; inserting a conduit into the first opening; rotatably adjusting a clamp having a first state and a second state about the annular wall when the clamp is in the first state; and transitioning the clamp from the first state to the second state to fix the clamp relative to the annular wall. The method can also include a clamp having a body and a brake defining a second opening and an actuator; wherein transitioning the clamp comprises rotating the actuator about an actuator axis generally parallel tot eh opening axis, thereby moving the brake relative to the body and causing the body to bear against the annular wall. Moving the brake may further comprise moving the brake along an axis transverse to the first opening. The method may also include an actuator comprising a cam member with an interface and transitioning the clamp may including coupling a tool to the actuator by relative motion of the tool and actuator along an actuator axis and rotating the cam member about the actuator axis. Transitioning the clamp may also include adjusting the actuator to change the position of a first arm extending from the body relative to a second arm extending from the body. The first arm can be separated from the second arm by a distance in the first state and transitioning the clamp from the first state to the second state can comprise urging the first arm and the second arm towards each other.

BRIEF DESCRIPTION OF THE DRAWINGS

A more complete appreciation of the subject matter of the present invention and the various advantages thereof can be realized by reference to the following detailed description, in which reference is made to the accompanying drawings.

DETAILED DESCRIPTION

Figure 1:
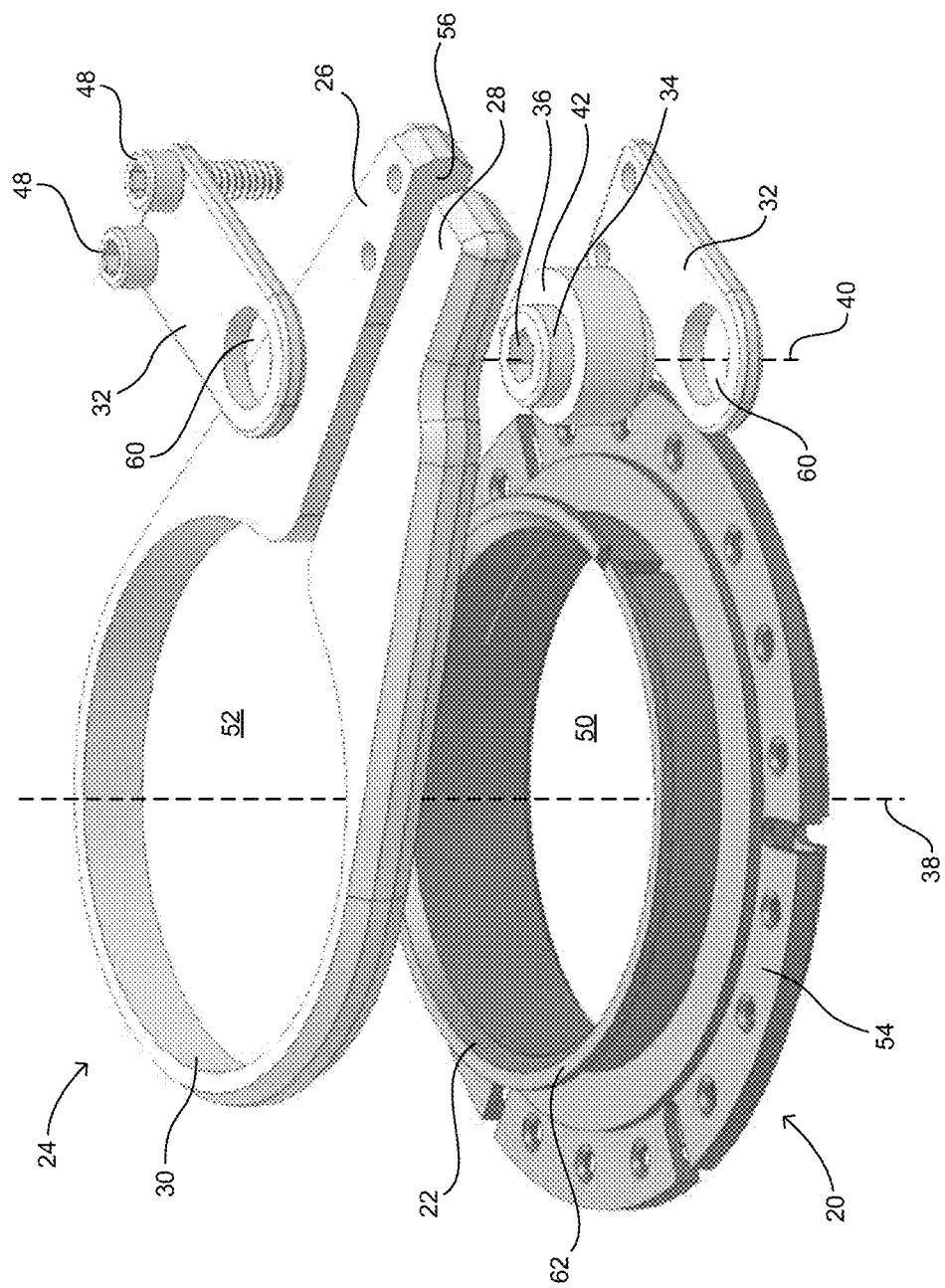
FIG. 1 illustrates an exploded perspective view of one embodiment of a connector ring assembly in accordance with the current invention.

A connector ring assembly 20 according to one embodiment of the invention includes an annular wall 22 defining an opening 50 extending along an opening axis 38. The opening 50 has a generally circular cross section to receive a conduit as explained in greater detail below. The opening could also be any shape desired, provided that it is able to receive the conduit. The annular wall 22 has a flange 54 extending therefrom in the embodiment shown in FIG. 1. It is believed that the flange can be used to secure the connector ring assembly to tissue (by suturing, stapling, etc.). A lip 62 extends around the free end of the annular wall 22 as best seen in FIG. 1. The annular wall also includes an annular wall relief cut 64.

Figure 2:
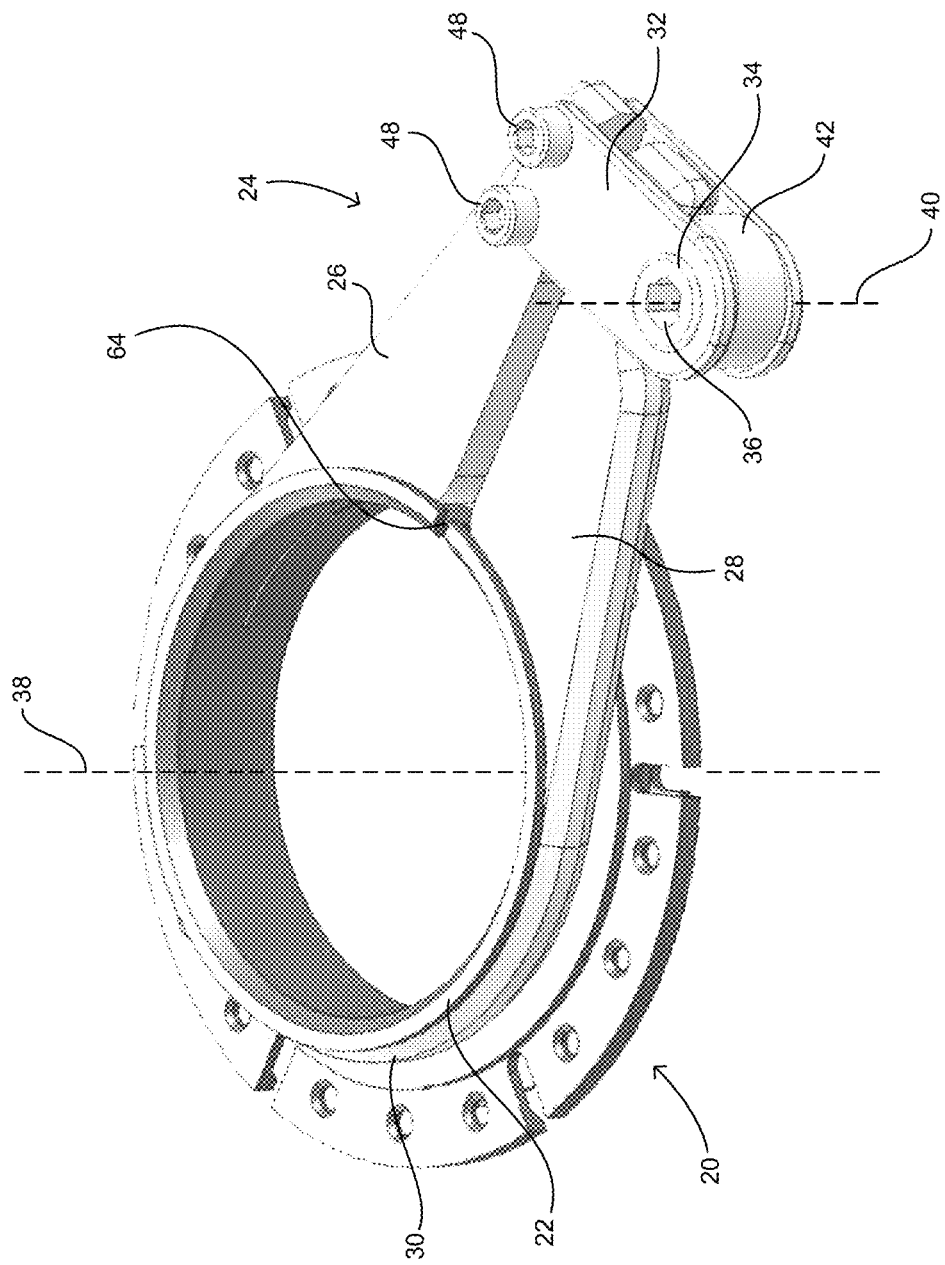
FIG. 2 illustrates an assembled perspective view of the connector ring assembly of FIG. 1.

The connector ring assembly 20 also includes a clamp 24 having a first arm 26 and a second arm 28 connected by a body 30 in the form of a flexible band. The arms 26, 28 and body 30 are depicted as a unitary member in FIG. 1 but could alternatively be separately formed elements that are joined (by welding, adhesive, connectors, etc.). The arms 26, 28 and body 30 collectively define a clamp opening 52 adapted to be positioned about the annular wall 22 as best seen in FIG. 2. As shown in FIG. 1, the arms are separated by a gap 56. As explained in more detail below, the width of the gap 56 decreases when the clamp 24 is transitioned from a first state to a second state.

The connector ring assembly 20 of FIGS. 1-4 also includes a spanning member 32 which extends from the first arm 26, across the gap 56, and beyond the second arm 28. The spanning member 32 is fixed to the first arm 26 by screws 48. However, the spanning member could also be connected to the first arm by welding, adhesive, etc. The spanning member and first arm could also be manufactured as a single piece.

Figure 3B:
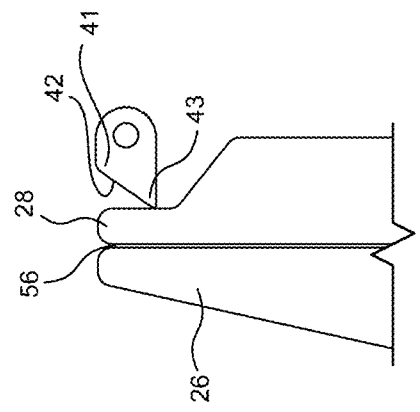
FIG. 3B illustrates a top view of the connector ring assembly of FIG. 1 in a second state.
Figure 3A:
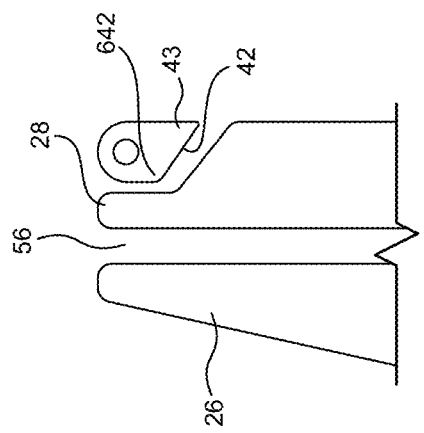
FIG. 3A illustrates a top view of the connector ring assembly of FIG. 1 in a first state.
Figure 4:
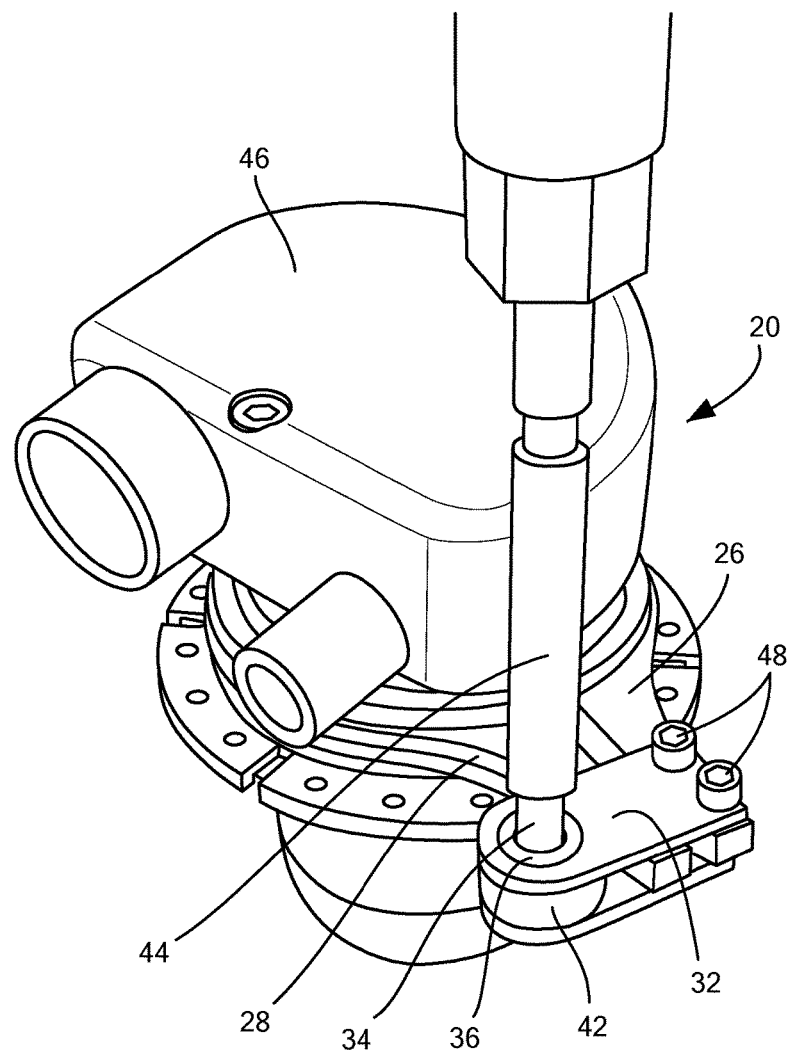
FIG. 4 illustrates a perspective view of the connector ring assembly of FIG. 3 coupled to a tool and a VAD connected to the connector ring assembly.

The spanning member 32 includes an orifice 60 to receive an actuator 34. When the actuator is within the orifice 60 as shown in FIG. 2, the actuator axis 40 is generally parallel to the opening axis 38. The actuator axis is offset from the opening axis. It is to be understood that the phrase generally parallel as used herein means within about 30 degrees of rotation about the opening axis and more preferably within about 15 degrees. It is believed that having an actuator axis generally parallel to the opening axis will allow the connector ring assembly to be implanted and transitioned from the first state to the second state through a single surgical accessway having a smaller size than that required for non-parallel actuator and opening axes. The actuator 34 has a cam surface 42 which lies at a non-uniform distance from actuator axis 40. As best seen in FIGS. 3A and 3B, cam surface 42 has a first region 41 where the cam surface is disposed at a first, relatively small distance from actuator axis 40, and a second region 43 where the cam surface is disposed at a second distance from the actuator axis, the second distance being greater than the first distance. The cam surface 42 tapers away from the actuator axis 40 in a circumferential direction around actuator axis 40, from first region 41 to second region 43. A cam surface which tapers along the actuator axis is also contemplated as shown, for example, in FIGS. 10-11. The actuator 34 is rotatable about the actuator axis 40 by a tool 44 (best seen in FIG. 4) to transition the clamp 24 from a first state to a second state as best seen in FIGS. 3A and 3B. The actuator 36 has an interface 36 which is arranged so that a tool 44 can be coupled to the actuator by relative motion between the actuator 34 and the tool 44 along the actuator axis 40. Merely by way of example, the interface can be a phillips screw head, slot, hex drive socket, a socket of the type commercially available under the trademark TORX, etc.

When the connector ring assembly 20 is fully assembled and the clamp opening 52 is positioned about the annular wall 22, the lip 62 and flange 54 maintain the alignment of the clamp 24 on the annular wall as shown in FIG. 2. The clamp 24 can rotate completely about the annular wall 22 when the clamp 24 is in the first state. The size of the clamp opening 52 is reduced when the clamp 24 is in the second state and the clamp 24 is fixed relative to, and bears against, the annular wall 22. The clamp 24 bearing against the annular wall 22 causes the annular wall to flex, the width of the annular wall relief cut 64 diminishes and the diameter of the opening 50 is reduced. An insert material (not shown), for example silicone or other flexible material, may occupy the void of the relief cut 64 when the clamp assembly is in the first state. The material is flexible to allow the relief cut to be reduced in size when the connector ring assembly transitions from the first state to the second state. It is believed that including the insert material helps reduce the possibility of leaks through the connector ring assembly.

Figure 5:
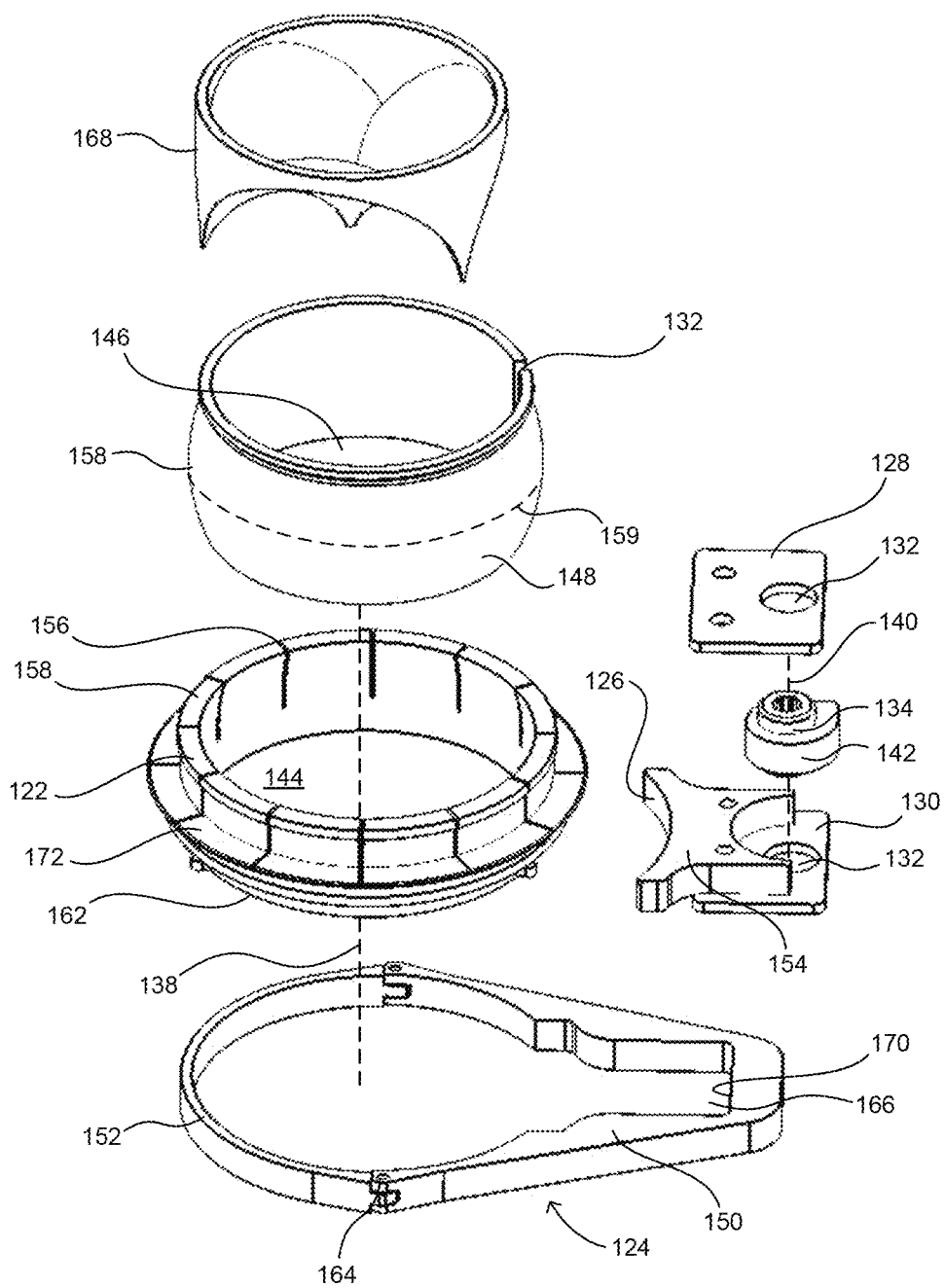
FIG. 5 illustrates an exploded view of one embodiment of a connector ring assembly in accordance with the current invention.

A connector ring assembly 120 according to another embodiment of the invention includes an annular wall 122 and a gimbal 158 as shown in FIGS. 5-8. The annular wall 122 defines an opening 144 which can be configured to receive a conduit or other element of a VAD (not shown). A plurality of relief cuts 156 extend from a proximal side 160 of the annular wall 122 toward a distal side 162 as best seen in FIG. 5. It is believed that having relief cuts which do not completely extend from the proximal side to the distal side may prevent the formation of leak paths which allow blood to leak through the connector ring assembly. The connector ring assembly shown in FIG. 5 has twelve relief cuts, however, any number of relief cuts are contemplated. The relief cuts may extend from the proximal side 160 toward the distal side 162 of the annular wall. In other embodiments, the relief cuts could stop proximal to the equator 159 of gimbal 158, thus eliminating any leak paths. The annular wall 122 includes a flange 172 and a lip on the proximal side to maintain the alignment of the clamp 124 on the annular wall. The distal side 162 of the annular wall 122 is configured to be connected to a detachable connector flange (not shown) which couples the annular wall to the tissue.

The gimbal 158 is adapted to be inserted into the opening 144 and is configured to receive a conduit or other element of a VAD (not shown) in the gimbal opening 146. The gimbal 158 has a semi-spherical contour which is received in the opening 144 so that the gimbal can pivot slightly to tilt the axis of the gimbal opening 146 relative to the annular wall 122. The gimbal 158 has a relief cut 132 which allows the gimbal to expand and contract beyond its resting configuration. The gimbal opening 146 is adapted to receive a valve 168 which can allow blood to flow in one direction while preventing flow in an opposite direction.

Figure 6:
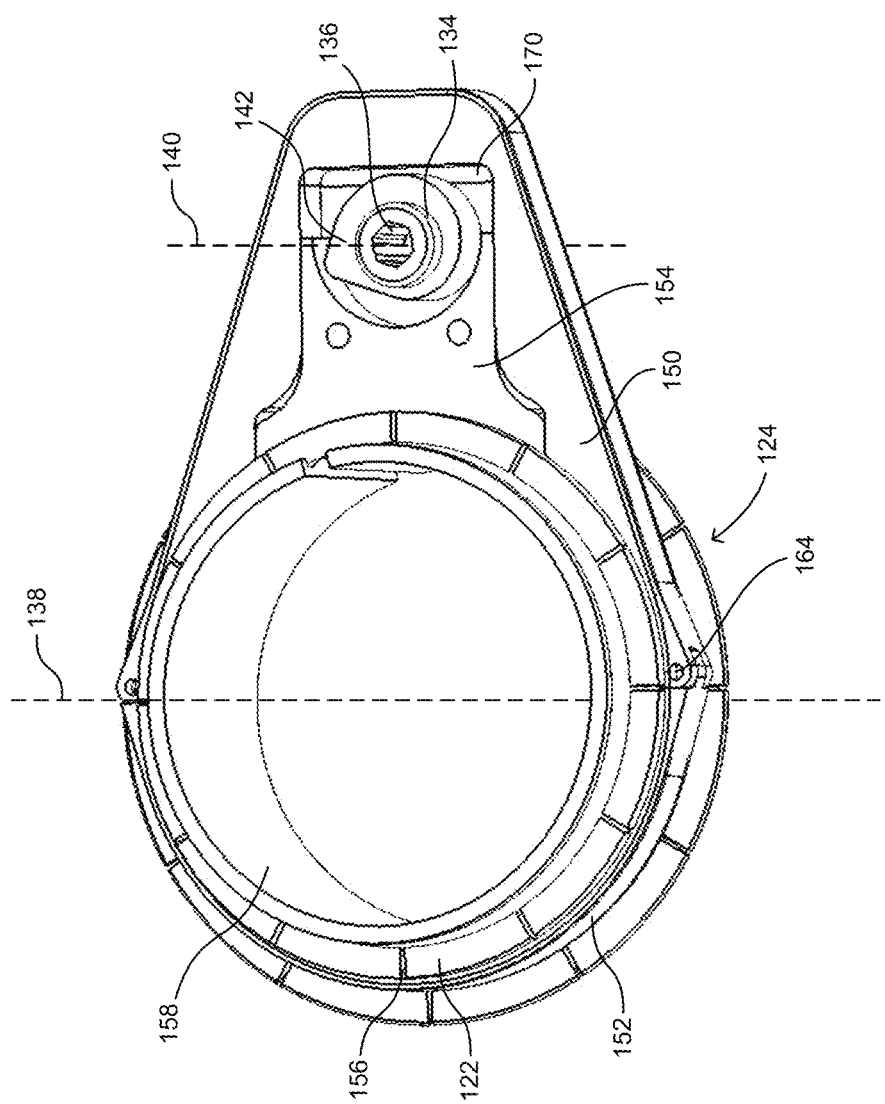
FIG. 6 illustrates a partially assembled view of the connector ring of FIG. 5 with an actuator in a first position.

The clamp 124 is has a first portion 150 and a second portion 152. The first and second portions 150, 152 are joined by a hinge 164 to form an internal arcuate surface with a radius similar to that of annular wall 122. A unitary member comprising the first and second portions is also contemplated. The first portion 150 includes a receiving area 166 for a brake 154. An actuation surface 170 forms part of the perimeter of the receiving area 166 as best seen in FIG. 6.

Figure 7:
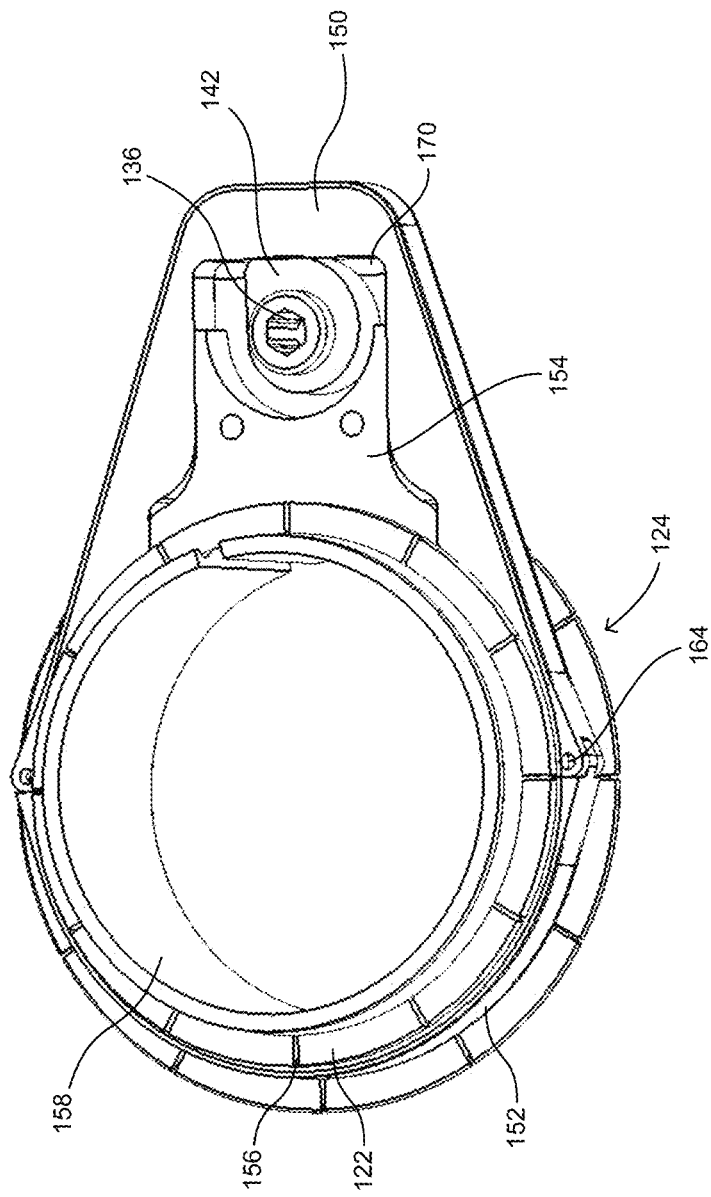
FIG. 7 illustrates a partially assembled view of the connector ring of FIG. 5 with an actuator in a second position.
Figure 8:
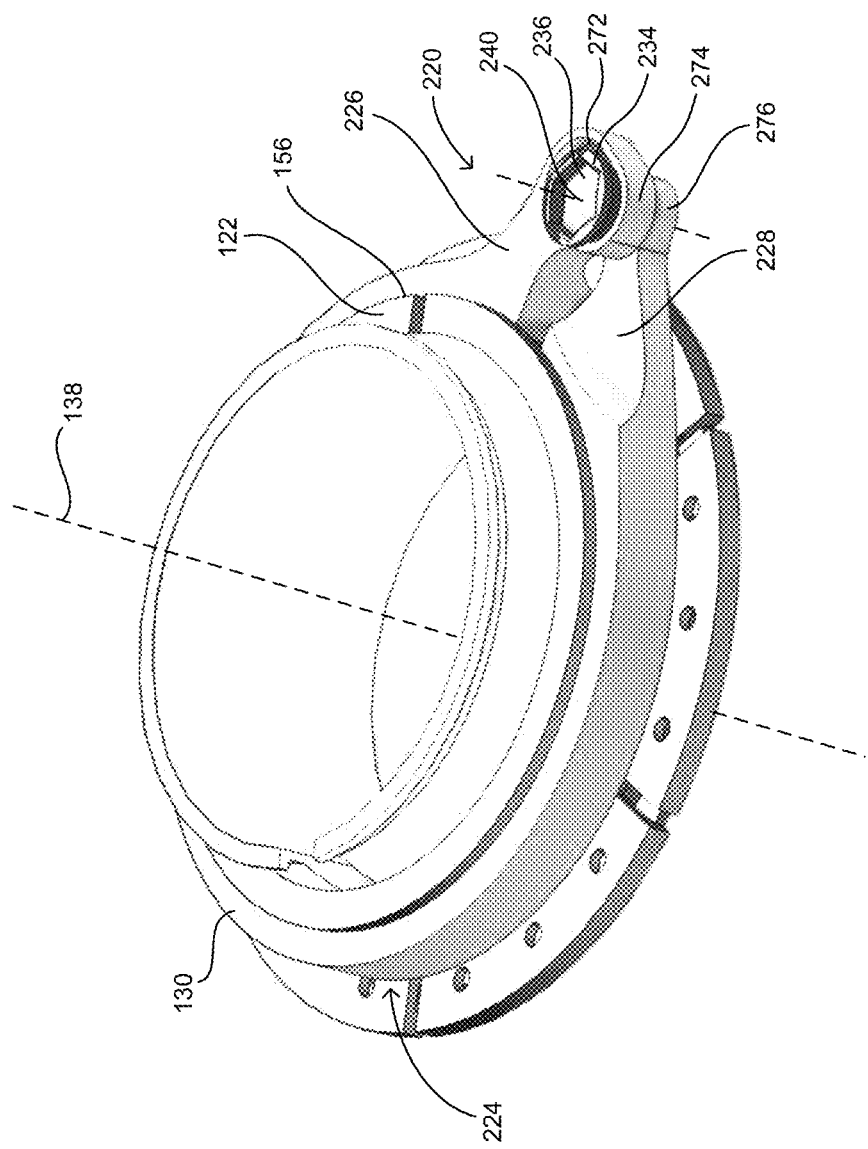
FIG. 8 illustrates a perspective view of one embodiment of a connector ring assembly in accordance with the current invention.
Figure 9:
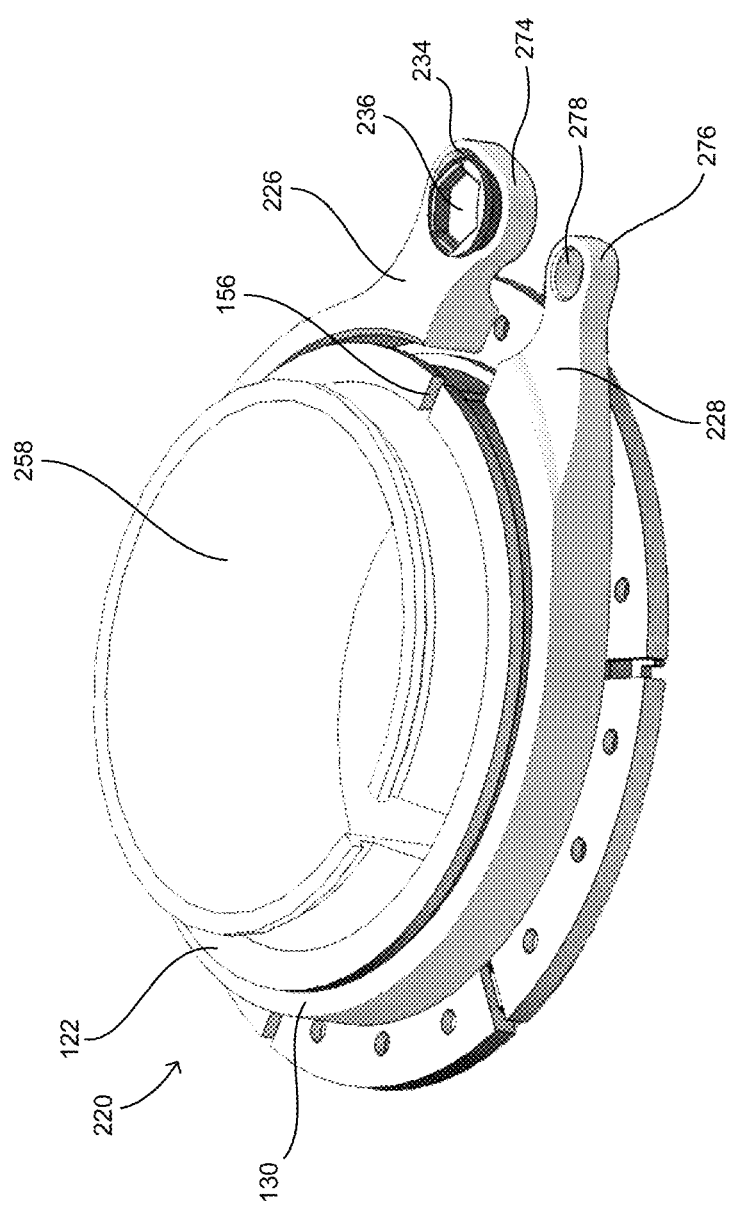
FIG. 9 illustrates a perspective view showing one configuration of clamp arms of the connector ring assembly of FIG. 8.

The brake 154 has a semi-circular surface 126 with a radius similar to that of the annular wall 122. The brake 154 is adapted to receive an actuator 134 between a top plate 128 and a bottom plate 130 which are coupled to the brake 154. The plates 128, 130 extend beyond the perimeter of the brake 154 to form a ledge to maintain the alignment of the brake 154 within the receiving area 166 while permitting sliding movement of the brake relative to the first portion 150. The top and bottom plate 128, 130 have a cutout 132 to receive an actuator 134 and permit rotational movement of the actuator 134 about an actuator axis 140. The actuator axis 140 is generally parallel to the opening axis 138. The actuator 134 has a cam surface 142 which tapers away from the actuator axis 140 as best seen in FIGS. 5-7. The actuator 134 includes an interface 136 to couple to a tool (not shown). The tool can be used to rotate the actuator 134, and thus the cam surface 142, into contact with the actuation surface 170 (best seen in FIGS. 6-7). Further rotation of the actuator after initial contact between the cam surface and the actuation surface drives the brake 154 towards the annular wall 122, and thus constrict the opening 144. This action also constricts the gimbal 158 which then bears against the VAD element. Rotation of the actuator also transitions the clamp from a first state where the clamp can rotate about the annular wall to a second state where the brake bears on the annular wall and the clamp is fixed with respect to the annular wall.

A connector ring assembly 220 according to yet another embodiment of the invention includes a clamp 224 as shown in FIGS. 8-12. Some aspects of the embodiment shown in FIGS. 8-12 are similar to the embodiment of FIGS. 1-4 and like reference numbers are used to refer to the common elements. The clamp 224 in FIGS. 8-12 includes a first arm 226 having a first end 274 and a second arm 228 having a second end 276. The first end 274 and the second end 276 overlap each other when the clamp is in a first state. However, any portion of the first arm and the second arm could overlap and still satisfy the purpose of the clamp. The clamp 224 is shown with the ends separated in FIG. 9 for illustration purposes.

Figure 10:
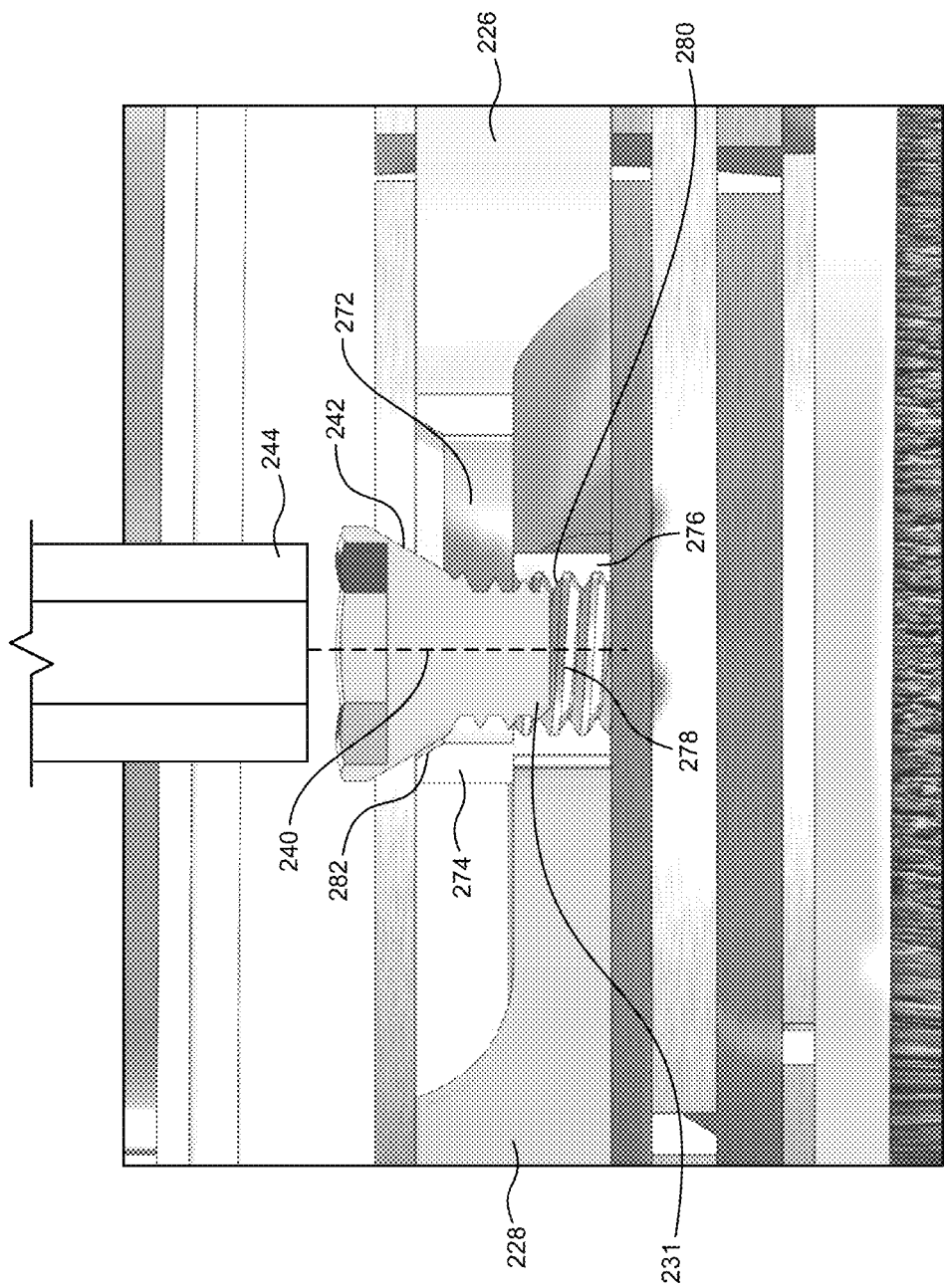
FIG. 10 illustrates a sectional view of the connector ring assembly and one embodiment of the actuator of FIG. 8.

The first end 274 includes a slot 272 to receive an actuator 234. As best seen in FIG. 10, one edge 282 of slot 272 has a sloped surface which cooperates with the actuator to cause relative motion between the actuator 234 and the first end 275. The second end 276 includes a hole 278 to receive the actuator 234. The hole 278 shown is narrower than the slot 272 and has straight sides.

Figure 11:
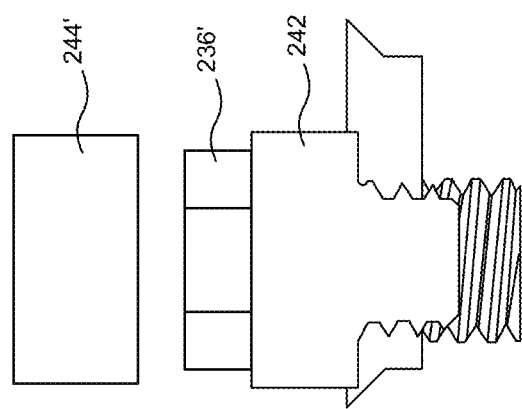
FIG. 11 illustrates a sectional view of the connector ring assembly and one embodiment of the actuator of FIG. 8.
Figure 12:
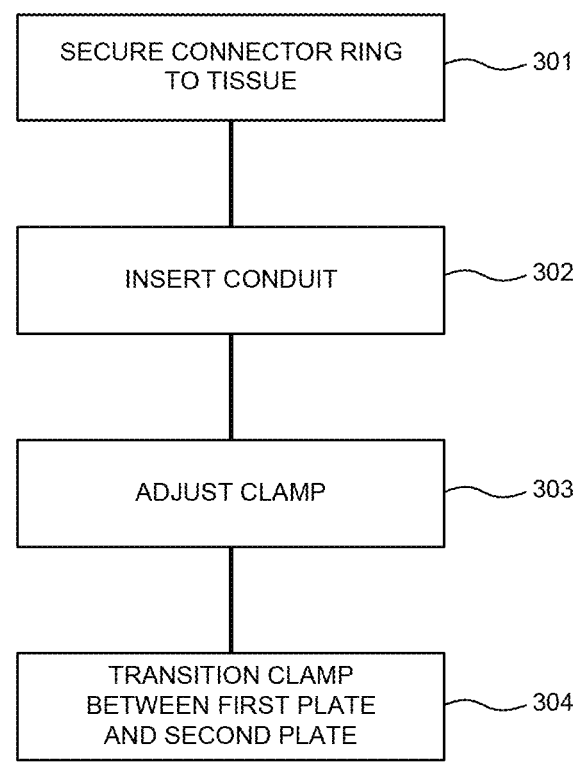
FIG. 12 is a flow chart illustrating one method of implanting a connector ring assembly in accordance with the present invention.

The actuator 234 includes a female interface 236 to couple to a tool 244 as best seen in FIG. 10. The actuator can have any number of interfaces including interface 236' which is a male interface to be received in a female end of tool 244' as best seen in FIG. 11. The actuator can also be held captive within the first arm or the second arm to prevent its accidental removal when the clamp is in use.

The actuator 234 has a cam surface 242 which tapers along the actuator axis 240 as best seen in FIG. 10. However, the actuator could also have a straight surface and the angled edge 282 of the slot 272 can provide the cam surface to move the first end 274 with respect to the second end 276 as shown in FIG. 11. The actuator 232 also has screw threads on a distal portion 231. The hole 278 in the second arm has corresponding threads. The threads on the distal portion of the actuator are engaged in the threads of hole 278 so that rotation of the actuator around its actuator axis 240 will move the actuator along the actuator axis relative to the clamp. The distal end 231 of the actuator could also be expanded after it is engaged with the threads of hole 278 to secure the actuator in place.

The screw arrangement provides a mechanical advantage when tightening the clamp. The threads on the screw can be configured to provide large axial force on the actuator for a given torque applied to the actuator. This large axial force in turn provides a large force between the cam surface 242 of the actuator and the cam surface 282, and thus provides a large lateral force to increase the overlap of the first and second ends and thereby transition the clamp to the second state. For example, this design can allow a user to transition the clamp with a torque of about 10-12 inch-ounces on the actuator. This arrangement minimizes overall torque on the connector ring assembly.

One method of attaching a connector ring assembly begins with securing the flange to tissue 301 with sutures, staples, rigid anchors, or similar devices for attachment. In those embodiments where the annular wall is separable from the flange, the step of securing the flange to tissue typically includes coupling the annular wall to the flange after securing the flange to the tissue. The clamp is coupled to the annular wall prior to securing the annular wall to the tissue. It is believed that providing the clamp secured to the annular wall prior to installation can help reduce the total time of surgery. In those embodiments where the annular wall of the connector ring is integral with the flange or permanently connected to the flange, the clamp may be provided on the annular ring before the connector ring is secured to the tissue. Because the clamp, in its first state, is freely rotatable about the annular ring, the clamp does not interfere with suturing or other procedures used to attach the flange to the tissue. The surgeon can simply swing the clamp away from a region of the flange while suturing or otherwise securing that region of the flange to the tissue, and then swing the clamp to a new position while securing the region previously covered by the clamp. However, the clamp could be coupled to the annular wall after it is installed, if desired. The gimbal desirably is also provided within the opening of the annular wall prior to attaching the annular wall to tissue.

In step 302, an element of the VAD is inserted into the gimbal (or opening of the annular wall if no gimbal is used). The element may be part of a VAD such as the pump housing, or may be another element such as an inlet conduit which can be coupled to a VAD. The gimbal allows the VAD element to be aligned at various orientations with respect to the opening axis while maintaining a leak proof seal between the annular wall and the conduit.

When the annular wall is secured to the heart via the flange, the clamp is in the first state and can be rotated 360° about the annular wall. The clamp can be adjusted 303 about the annular wall before and after the conduit is inserted into the gimbal.

In step 303, a tool is then coupled to the interface on the actuator by relative motion between the actuator and tool along the actuator axis. The actuator is then rotated to transition the clamp from the first state to the second state 304. This action tightens the clamp and secures the VAD element in place.

Depending on the design of the clamp used, rotating the actuator transitions the clamp from the first state to the second state by reducing the distance separating the first and second arms (best seen in FIGS. 3A-3B and 10) or translating the brake along an axis and into contact with the annular wall (best seen in FIGS. 6-7). Regardless of the clamp embodiment used, the clamp bears on the annular wall in the second state and is rotationally fixed relative to the annular wall. The annular wall relief cuts are reduced in size and the diameter of the opening constricts such that the annular wall tightens on the gimbal which, in turn, secures the conduit within the gimbal opening.

Although the invention herein has been described with reference to particular embodiments, it is to be understood that these embodiments are merely illustrative of the principles and applications of the present invention. Merely by way of example, features of the various embodiments discussed above may be combined with one another. For example, the male interface on the actuator (FIG. 11) can be used in any of the embodiments discussed above. Also, a gimbal such as that shown in FIG. 5, can be used in the embodiments discussed above, with or without the valve depicted in FIG. 5. It is therefore to be understood that numerous modifications may be made to the illustrative embodiments and that other arrangements may be devised without departing from the spirit and scope of the present invention as defined by the appended claims.

The invention claimed is:

1. A connector ring assembly comprising:
    an annular wall defining a first opening adapted to receive a conduit, the first opening having an opening axis;
    a clamp having a body and a first arm and a second arm coupled to each other by the body, the first arm and the second arm defining a distance therebetween extending away from body and entirely along the first arm and the second arm, the clamp engaging the annular wall and defining a second opening co-axial with the first opening, the clamp operably configured to rotate relative to the annular wall in a first state and remain fixed relative to the annular wall in a second state, and the distance between the first arm and second arm in the first state being greater than the distance between the first arm and second arm in the second state;
    an actuator disposed substantially parallel with respect to the annular wall and the clamp, the actuator adapted to transition the clamp between the first state and the second state; and
    an actuator receiver defining an actuator opening including the actuator disposed therein, the actuator opening having an actuator axis generally parallel to the opening axis.

2. The connector ring assembly of claim 1, wherein the actuator axis is offset from the opening axis.

3. The connector ring assembly of claim 1, wherein at least a portion of the first and second arms overlap.

4. The connector ring assembly of claim 3, wherein the first arm and the second arm form a unitary member which includes a flexible band.

5. The connector ring assembly of claim 1, wherein the diameter of the second opening defined by the clamp body in the first state is larger than an outer diameter of the annular wall and the clamp body bears on the outer diameter of the annular wall in the second state.

6. The connector ring assembly of claim 3, wherein:
    the actuator receiver is a spanning member adapted to receive the actuator and coupled to one of the first arm and the second arm and extending past the other of the first arm and the second arm.

7. The connector ring assembly of claim 3, wherein the actuator further comprises a cam rotatable about the actuator axis and rotation of the cam urges at least one of the first arm and the second arm toward the other of the first arm and the second arm.

8. The connector ring assembly of claim 7, wherein the actuator is threadingly engaged with the clamp body for movement along the actuator axis upon rotation of the cam about the actuator axis.

9. The connector ring assembly of claim 8, wherein the actuator has a sloping cam surface.

10. The connector ring assembly of claim 1, further comprising an interface on the actuator configured to engage a tool by relative motion of the tool and the actuator along the actuator axis.

11. The connector ring assembly of claim 1, wherein the annular wall comprises at least one relief cut extending from a proximal side of the annular wall toward a distal side of the annular wall.

12. The connector ring assembly of claim 11, wherein the at least one relief cut has a first width when the clamp is in the first state and has a second width smaller than the first width when the clamp is in the second state.

13. The connector ring assembly of claim 1, wherein the clamp includes a brake separate from the clamp body and adapted to be moved by the actuator to transition the clamp from the first state to the second state.

14. The connector ring assembly of claim 13, wherein the actuator comprises a rotatable cam, and rotation of the cam moves the brake relative to the body to reduce the diameter of the second opening.

15. The connector ring assembly of claim 13, wherein the body comprises first and second portions connected by at least one hinge.

16. The connector ring assembly of claim 1, further comprising a gimbal adapted to be placed within the first opening to receive a conduit at a plurality of angles relative to the opening axis.

\* \* \* \* \*